(12) United States Patent
Baru et al.

(10) Patent No.: US 6,930,087 B2
(45) Date of Patent: Aug. 16, 2005

(54) PHARMACEUTICAL COMPOSITION COMPRISING FACTOR VIII AND NEUTRAL LIPOSOMES

(75) Inventors: Moshe Baru, Pardes Hana (IL); Liliana Bar, Rehovot (IL); Israel Nur, Moshav Timurim (IL)

(73) Assignee: Opperbas Holding B.V., Amsterdam (NL)

( * ) Notice: Subject to any disclaimer, the term of this patent is extended or adjusted under 35 U.S.C. 154(b) by 118 days.

(21) Appl. No.: 10/327,970

(22) Filed: Dec. 26, 2002

(65) Prior Publication Data

US 2003/0134778 A1 Jul. 17, 2003

Related U.S. Application Data

(62) Division of application No. 09/673,412, filed as application No. PCT/IL99/00217 on Apr. 23, 1999, now Pat. No. 6,593,294.

(30) Foreign Application Priority Data

Apr. 27, 1998 (IL) ................................. 124224

(51) Int. Cl.[7] .......................... A61K 38/00; C12N 15/88
(52) U.S. Cl. ........................... 514/2; 514/802; 514/834; 424/450; 530/350; 530/380; 530/383
(58) Field of Search ........................... 514/2, 802, 834; 424/450; 530/350, 380, 383

(56) References Cited

U.S. PATENT DOCUMENTS

| | | | |
|---|---|---|---|
| 4,348,384 A | 9/1982 | Horikoshi et al. | 424/101 |
| 5,013,556 A | 5/1991 | Woodle et al. | 424/450 |
| 5,527,528 A * | 6/1996 | Allen et al. | 424/178.1 |

FOREIGN PATENT DOCUMENTS

| | | | |
|---|---|---|---|
| EP | 0 689 428 B1 | | 1/1996 |
| WO | WO 80/01456 | | 7/1980 |
| WO | WO 91/12021 | * | 8/1991 |
| WO | WO 94/21235 | | 9/1994 |

OTHER PUBLICATIONS

Sahli et al., "Interactions of poly(lactic acid) and poly(lactic acid–co–ethylene oxide) nanoparticles with the plasma factors of the coagulation system", BIOMATERIALS 1997, vol., 18, No. 4, pp. 281–288.

Blume et al., "Specific targeting with poly(ethylene glycol)–modified liposomes: coupling of homing devices to the ends of the polymeric chains combines effective target binding with long circulation times" BIOCHIMICA ET BIOPHYSICA ACTA, 1449 (1993) 180–184.

Barrowcliffe et al., "Binding to phospholipid protects factor VIII from inactivation by human antibodies" 1983, J. Lab. Clin. Med. 101:34–43.

Kemball–Cook, Interaction of Factor VIII with Phospholipids: Role of Composition and Negative Charge, 1992, Thromb. Res. 67:57–71.

Bloom et al., "Haemostasis and Thrombosis", Biochemistry of Prothrombin Activation, pp. 179–180, 1987.

Arakawa et al., "Mechanism of Poly(ethylene glycol) Interaction with Proteins", BIOCHEMISTRY, vol. 24, No. 24, 1985, pp. 6756–6762.

Lee et al., "Preferential Solvent Interactions between Proteins and Polyethylene Glycols", Journal of Biological Chemistry, vol. 256, No. 2, Jan. 25, 1981, pp. 625–631.

* cited by examiner

*Primary Examiner*—Jon Weber
*Assistant Examiner*—Holly Schnizer
(74) *Attorney, Agent, or Firm*—Oliff & Berridge, PLC

(57) ABSTRACT

A pharmaceutical composition for parenteral administration comprising a therapeutically effective amount of a protein or polypeptide and substantially neutral colloidal particles. The particles comprise approximately 1–20 mole percent of an amphipathic lipid derivatized with a biocompatible hydrophilic polymer which carriers substantially no net charge.

The protein or polypeptide is capable of externally binding the colloidal particles, or is capable of binding polyethylene glycol, and is not encapsulated in the colloidal particles. A preferred protein is factor VIII, whose half-life is extended and which is protected from serum inhibitor antibodies by injecting it as a component of the composition.

17 Claims, 1 Drawing Sheet

PHARMACEUTICAL COMPOSITION COMPRISING FACTOR VIII AND NEUTRAL LIPOSOMES

FIELD OF THE INVENTION

The present invention relates to a stable pharmaceutical formulation for the slow release of coagulation promoting substances for the treatment of blood coagulation disorders.

BACKGROUND OF THE INVENTION

Hemophilia A is one of the most frequently occurring inherited coagulation disorders. Patients with hemophilia A are prone to frequent hemorrhages as a result of one or more misfunctions of the coagulation system. One of the causes of hemophilia is a shortage of Factor VIII (FVIII) in the blood. This problem can be treated with Factor VIII concentrates. However, in about 15% of the patients the occurrence results of Factor VIII neutralizing antibodies, so-called inhibitors, whereby a therapy with Factor VIII concentrates is hardly possible.

Two basic approaches have been described in the literature to protect FVIII from inactivation by inhibitors.

WO/80/01456 to Hemker discloses a pharmaceutical composition suitable for oral administration comprising FVIII incorporated within liposomes of 0.5–1.0 microns formed from phospholipids. The phospholipids have a net charge, and the FVIII is incorporated between the layers of the liposome. It is claimed that FVIII levels in the plasma remained above about 5% of the normal value for a period of 50 hours.

U.S. Pat. No. 4,348,384 to Horikoshi states that a composition as described in Hemker was prepared, but did not give satisfactory results. Therefore, Horikoshi incorporates a protease inhibitor into the liposome together with FVIII, in order to protect it from proteolysis. 3% of the normal plasma levels of FVIII were obtained over a period of 6 hours.

U.S. Pat. No. 5,013,556 to Woodle discloses a liposome composition for use in delivering various drugs via the bloodstream. The liposome contains between 1–20 mole percent of an amphipathic lipid derivatized with a polyalkylether. Here also, the drug compound is entrapped within the liposome. These liposome compositions are available commercially under the name of Stealth® vesicles (SUV's, small unilamellar vesicles comprised of phospholipid and polyethylene glycol (PEG) covalently bound to phospholipid).

A further problem with this approach is that liposomes having a large diameter have a short half-life. Therefore, the liposomes must be downsized under high pressure, which can affect protein activities as in coagulation factors V and VIII.

In a second approach, Barrowcliffe, T. W., et al. (1983) J. Lab. Clin. Med. 101:34–43 teaches that mixing FVIII with phospholipid extracted from human and/or animal brain imparts significant protection to the FVIII in vitro. In this approach, the phospholipid is bound to the FVIII rather than encapsulating it. Kemball-Cook, G. and Barrowcliffe, T. W. (1992) Thromb. Res. 67:57–71, teaches that a negatively-charged phospholipid surface is necessary for FVIII binding. Negatively charged phosphatidyl serine and phophatidic acid were found to be highly active in binding to FVIII, while phosphatidyl choline was inactive. However, negatively-charged phospholipids are toxic, and those derived from brain tissue may carry pathogenic agents.

EP 689,428 discloses a liposome composition comprising liposomes having an outer surface layer of hydrophilic polymer chains. A polypeptide or polysaccharide effector molecule is covalently attached to the distal ends of the polymer chains by activation of the lipid anchor prior to effector coupling.

SUMMARY OF THE INVENTION

It is an object of the present invention to provide a pharmaceutical composition comprising a protein or polypeptide for therapeutic treatment. In particular, it is an object of the present invention to provide a pharmaceutical composition comprising FVIII for the treatment of blood coagulation disorders.

It is a further object of the invention to provide FVIII in a form having an extended half-life in the bloodstream.

It is a still further object of the invention to provide a method for treating patients suffering from blood coagulation disorders, particularly hemophilia, and most particularly those having FVIII inhibitors.

In one aspect of the present invention there is provided a pharmaceutical composition for parenteral administration comprising a therapeutically effective amount of coagulation factor VIII (FVIII) and substantially neutral colloidal particles, the particles comprising 1–20 mole percent of an amphipathic lipid derivatized with a biocompatible hydrophilic polymer, the polymer carrying substantially no net charge, wherein the FVIII is not encapsulated in the colloidal particles.

The present invention is based on the surprising and unexpected finding that neutral phospholipids derivatized with a bio-compatible hydrophilic polymer can be used to bind FVIII and protect it from inhibitors in the bloodstream. This provides a significant advantage over the prior art compositions, since the phospholipids used are synthetic and non-toxic, and can therefore be used in vivo for therapeutic treatment. Furthermore, the liposome does not encapsulate the FVIII so that smaller sized liposomes can be used which have a longer half-life in vivo, since they are not removed by the reticuloendothelial system (RES). As will be described below in greater detail, FVIII interacts non-covalently with the polymer chains on the external surface of the liposomes, and no chemical reaction is carried out to activate the polymer chains, unlike the composition disclosed in EP 689,428.

In the present specification, the terms "substantially neutral" and "substantially no net charge" mean neither positively nor negatively charged. However, a very low measured charge within experimental error of zero is included within the meaning of the above terms.

The term "therapeutically effective amount" is to be understood as referring to an amount of FVIII which results in a level of FVIII in the bloodstream having a desired therapeutic effect. Such an amount can be experimentally determined by administering compositions comprising different amounts of FVIII and measuring the level in the blood at various times after administration.

The amphipathic lipid used to prepare the colloidal particles is preferably a phospholipid, and may be obtained from either natural or synthetic sources. A most preferred phospholipid is phosphatidylcholine, most preferably egg-phosphatidylcholine.

The biocompatible hydrophilic polymer may include polymers from the polyalkylether, polylactic or polyglycolic acid families. Preferably, the polymer is polyethylene glycol (PEG). The purpose of the polymer is to sterically stabilize the SUVs, thus preventing fusion of the vesicles in vitro, and allowing the vesicles to escape adsorption by the RES in vivo. The polymer will preferably have a molecular weight of between about 1000 to about 5000 daltons, most preferably approximately 2000 daltons.

The colloidal particles will preferably have a mean particle diameter of between about 0.05 to about 0.4 microns, most preferably about 0.1 microns. This is to increase their circulation time in vivo and prevent their adsorption by the RES. The amphipathic lipid comprises approximately 1 to about 20 mole % of the particles, preferably approximately 1–5%, most preferably 5%.

A variety of known coupling reactions may be used for preparing vesicle forming lipids derivatized with hydrophilic polymers. For example, a polymer (such as PEG) may be derivatized to a lipid such as phosphatidylethanolamine (PE) through a cyanuric chloride group. Alternatively, a capped PEG may be activated with a carbonyl diimidazole coupling reagent, to form an activated imidazole compound. Other reactions are well known and are listed, e.g. in the aforementioned U.S. Pat. No. 5,013,556, whose contents are incorporated herein by reference.

The FVIII used in the composition of the invention is commercially available. It may be from a natural human source, or, preferably, it may be recombinantly prepared. Recombinant FVIII is commercially available, for example, Antihemophilic Factor (Recombinant), rFVIII-SQ (Pharmacia), and Kogenate, Miles Inc., Pharmaceutical Division, Elkhart, Ind., U.S.A., among other suppliers.

The composition of the invention is administered parenterally, preferably iv. The prior art compositions were intended for oral use only, due to side effects caused during injection by the liposome composition. The composition of the invention, on the other hand, is not toxic by injection, apparently due to the lack of charge, among other causes. Amounts of up to 0.5 gm/Kg body weight of colloidal particles according to the invention have been injected without detectable toxic symptoms. The dose is expected to be in the approximate range of 25–75 i.u./Kg. body weight. The particle to FVIII ratio (w/unit FVIII) will preferably be between about 0.1 mg/unit and about 10 mg/unit, and most preferably, approximately 1 mg/unit. Although the free form of FVIII:C has a half-life of less than 2 hours (FVIII measured by clotting activity) in mice, FVIII administered in the composition of the invention is expected to be effective for at least 24 hours, which is the period of effective activity of the coagulation promoting compound. The composition of the invention is expected to be effective in "on demand" and prophylactic treatment of hemophilia patients, and particularly those patients who have developed FVIII inhibitor antibodies.

The effectiveness of FVIII contained in the composition of the invention may be determined by a chromogenic assay which determines FVIII activity by two consecutive steps: (1) the FVIII-dependent conversion of Factor X to Factor Xa in a coagulation-factor reagent composed of purified components, and (2) the enzymatic cleavage of a chromogenic Factor Xa substrate to yield a chromophore which can be quantified spectrophotometrically. Under appropriate assay conditions, there exists a linear relationship between the rate of Factor Xa formation and the FVIII concentration. In addition, FVIII activity may be determined by a one-stage clotting assay. This assay determines FVIII activity by the conversion of prothrombin to thrombin, which subsequently cleaves fibrinogen to form a clot composed of fibrin. FVIII activity in hemophillic mice may also be determined by measuring the survival of the mice following a tail cut.

In a further aspect of the invention, there is provided a pharmaceutical composition for parenteral administration comprising a therapeutically effective amount of a protein or polypeptide and substantially neutral colloidal particles, said particles comprising approximately 1–20 mole percent of an amphipathic lipid derivatized with a biocompatible hydrophilic polymer, said polymer carrying substantially no net charge, wherein said protein or polypeptide is selected from the group consisting of: (a) proteins or polypeptides capable of externally binding said colloidal particles; and (b) proteins of polypeptides capable of binding polyethylene glycol (PEG), and wherein said protein or polypeptide is not encapsulated in said colloidal particles.

The term "proteins or polypeptides capable of externally binding said colloidal particles" includes proteins and polypeptides which, similarly to FVIII, bind to membranes comprising phosphatidylcholine:phosphatidylserine (PC:PS) (see Haemostasis and Thrombosis. Arthur L. Bloom and Duncan P. Thomas (eds) (1987) Churchill Livingstone, pg. 179–180). Non-limiting examples of such proteins are coagulation factors such as prothrombin, Factor X and Factor V.

The term "proteins or polypeptides capable of binding polyethylene glycol" includes proteins and polypeptides which bind to PEG or derivatives of PEG by any non-covalent mechanism, such as ionic interactions, hydrophobic interactions, hydrogen bonds and Van der Waals attractions (Arakawa, T. and Timasheff, S. N. (1985) Biochemistry 24:6756–6762; Lee, J. C. and Lee, L. L. Y. (1981) J. Biol. Chem. 226:625–631).

DETAILED DESCRIPTION OF A PREFERRED EMBODIMENT

Figure 1:
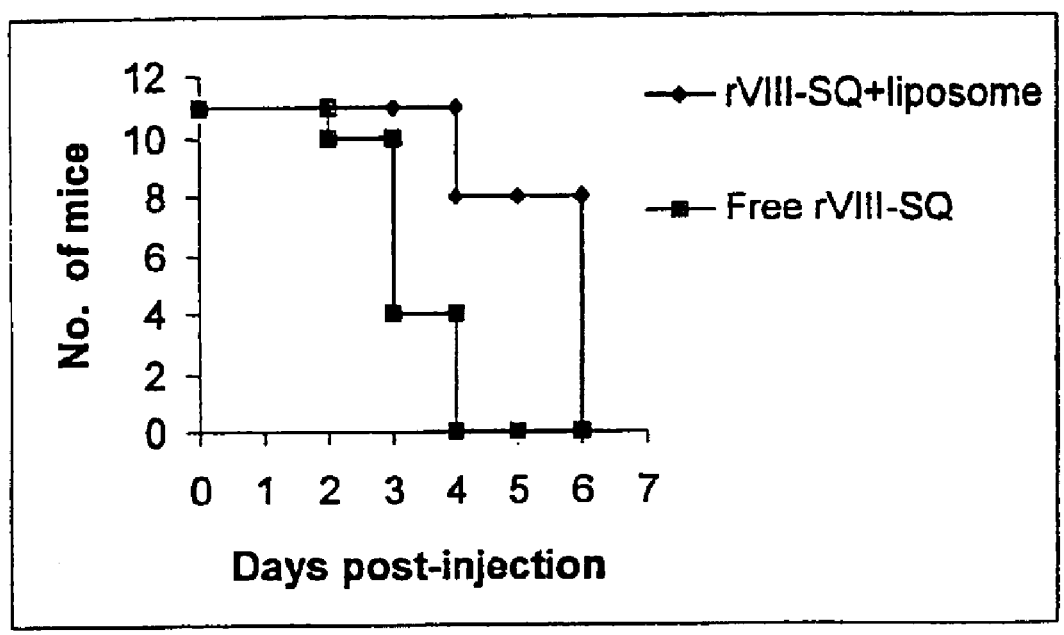
FIG. 1 illustrates survival of hemophilic mice injected with FVIII following a tail cut at various time periods post-injection.

In order to understand the invention and to see how it may be carried out in practice, preferred embodiments will now be described, by way of non-limiting example only, with reference to the accompanying drawing (FIG. 1).

EXAMPLES 1–3

Methods and Materials

1. Egg phosphatidylcholine (E-PC) liposomes

A tert-butanol solution of egg phosphatidylcholine (E-PC) was prepared by dissolving 2.0 gr. E-PC, 1.9 mg α-tocopherol and fluorescein-labeled phosphatidylethanolamine (1:1000 lipid molar ratio) in 18 ml tert-butanol.

The organic solvent was removed from the lipidic mixture by lyophilization and the lipids reconstituted in water to 10% w/v. The obtained liposomes were reduced in size by extruding them through a series of polycarbonate (PC) filters (0.4 μm, 0.2 μm, 0.1 μm and 0.05 μm) using the Liposofast-Basic or Liposofast-50 extruder (Avestin) to obtain liposomes of an average size of 0.1 μm.

2. Egg phosphatidylcholine/polyethyleneglycol-phosphatidyl Ethanolamine (E-PC/PEG-PE) Liposomes A tert-butanol solution of egg phosphatidylcholine (E-PC) and polyethyleneglycol-phosphatidyl ethanolamine (PEG-PE) was prepared by mixing 0.73 gr. E-PC, 0.185 gr. PEG-PE, 0.86 mg α-tocopherol and fluorescein labeled phosphatidylethanolamine (1:1000 lipid molar ratio) in 18 ml tert-butanol.

The organic solvent was removed from the lipidic mixture by lyophilization and then reconstituted in water to 10% w/v. The obtained liposomes were reduced in size as described in 1 above to obtain liposomes of an average size of 0.1 μm.

3. Egg phosphatidylcholine-phosphatidyl glycerol (E-PC/PG) Liposomes

A tert-butanol solution of egg phosphatidylcholine (E-PC) and phosphatidyl glycerol (PG) was prepared by mixing 0.822 gr. E-PC, 0.0924 gr. PG, 0.86 mg α-tocopherol and phosphatidylethanolamine fluorescein labeled (1:1000 lipid molar ratio) in 18 ml tert-butanol.

The organic solvent was removed from the lipidic mixture by lyophilization and then reconstituted in water to 10% w/v. The obtained liposomes were reduced in size as described in 1 above to obtain liposomes of an average size of 0.1 μm.

4. Reconstitution of the human recombinant factor VIII:

Kogenate (rFVIII formulated with human albumin, Bayer) lots 70K026 and 70K027, were used in the following examples. One vial containing about 500 IU of FVIII activity was reconstituted with 2 ml water and allowed to solubilize. 200 μl aliquots were frozen at −20° C. until use.

For the preparation of albumin-depleted Kogenate, lot # 70K027 was used. 10 vials of Kogenate were reconstituted in 20 ml water and chromatographed on a hydrophilic silica gel (3–10 μm beads). Fractions of 10 ml were collected and the protein and FVIII:Ag activities were monitored. A 50% recovery in FVIII:Ag activity was found in one peak of fractions 4–6 and another of fractions 8–14. Since the protein assay gave a peak at fractions 9–12, fractions 4–6 were pooled, aliquoted and lyophilized for further use.

5. Hemophilic mice prepared as described in Bi, L., et al. (1995) Nature Genetics 10:119–121, were used.

6. FVIII:Ag activity was determined using a FVIII chromogenic assay commercially available from Dade AG, Dudingen, Switzerland.

7. Preparation of Composition and Injection to Hemophiliac Mice

A liposomal aliquot was mixed with a predetermined volume of FVIII to obtain a FVIII:Ag activity of 5–10 IU/ml and rolled at RT to achieve homogeneity.

8. Groups of 5–10 hemophiliac mice were injected IV bolus through the tail vein, with 200 or 400 μl of the mixture. The mice were bled from the eye at regular time intervals (1 h, 4 hs, 8 hs, 24 hs, 32 hs and 48 hs) and the FVIII:Ag activities in the plasma were followed.

9. The pharmacokinetics of FVIII was determined from the results by using the RSTRIP computation software to obtain the initial FVIII:C activity ($A_0$) and the half-life time ($T_{1/2}$) of the factor in the mice blood circulation.

Results

1. Effect of Lipid Composition on the Half-Life of Factor VIII.

Liposomes of 0.05 μm comprising E-PC, E-PC/PEG-PE and E-PC/PG were prepared, mixed with Kogenate in a 72:1 lipid to protein (w/w) ratio and injected into hemophiliac mice. As a control, Kogenate was diluted in saline and injected into the mice in the same manner as the liposomal mixtures. The pharmacokinetic parameters were determined as described above, and the results are summarized in the following table:

TABLE 1

Effect of lipid composition on the half-life of FVIII

| Lipid composition | $A_0$* (IU/ml) | $T_{1/2}$ (hs) | no. of mice |
|---|---|---|---|
| Control | 2.22 | 4.51 | 18 |
| E-PC/PEG-PE | 3.20 | 7.84 | 10 |
| E-PC | 1.01 | 2.33 | 10 |
| E-PC/PG | Not-detectable | not-detectable | 10 |

*$A_0$ = initial concentration of FVIII:C

It can be seen from the table that liposomes containing E-PC/PEG-PE were the most effective since both the initial FVIII activity and the half-life time were higher for this composition than for Kogenate or Kogenate-liposome mixtures where the liposomes were composed of E-PC/PG or E-PC only.

Moreover, 40% of the mice injected with free FVIII and 100% of the mice injected with FVIII/PC complex did not exhibit any recovery of FVIII chromogenic activity, while only 10% of the mice injected with FVIII/PC+PEG exhibited the same phenomena 60 min. after injection.

2. Effect of Lipid/Protein Ratio on the Half-Life of Factor VIII.

Various lipid to protein ratios in the liposome composition were obtained by mixing various aliquots of liposomes of 0.05 μm comprising E-PC/PEG-PE with Kogenate. These were injected into hemophiliac mice. As a control, Kogenate was diluted in saline and injected into the mice in the same manner as the liposomal mixtures. The pharmacokinetic parameters were determined as described above, and the results are summarized in the following table:

TABLE 2

Effect of lipid to protein ratio on the half-life of FVIII

| lipid/prot. (w/w) | $A_0$ (IU/ml) | $T_{1/2}$ (hs) | no. of mice |
|---|---|---|---|
| 134 | 2.26 | 3.3 | 10 |
| 32 | 1.61 | 1.91 | 10 |
| 5.3 | 3.12 | 1.64 | 10 |
| 0.89 | 2.69 | 1.5 | 10 |
| Control | 2.22 | 1.5 | 18 |

It can be seen from Table #2 that increasing the lipid/protein ratio increases the half-life time of FVIII in the blood circulation in the hemophiliac mice. The differences in the initial FVIII:C activities appear not to be related to the lipid/protein ratio.

3. Effect of Different Factor VIII Sources

SUVs of 0.05 μm were prepared containing E-PC and PEG-PE (94:6 mol %), mixed with FVIII concentrates from various sources (Kogenate, Baxter and Omrixate) in a 72:1 lipid to protein ratio and injected into hemophiliac mice. As a control, each FVIII concentrate from the various sources was diluted in saline and injected into the mice in the same manner as the liposomal mixtures. The pharmacokinetic parameters were determined as described above, and the results are summarized in the following table:

TABLE 3

Effect of factor FVIII source on the half-life of FVIII

| source | $A_0$ (IU/ml) | $T_{1/2}$ (hs) |
|---|---|---|
| Kogenate | 2.22 | 4.51 |

TABLE 3-continued

Effect of factor FVIII source on the half-life of FVIII

| source | $A_0$ (IU/ml) | $T_{1/2}$ (hs) |
|---|---|---|
| Kogenate + SUV's | 3.36 | 8.60 |
| Baxter | 1.36 | 3.83 |
| Baxter + SUV's | 1.08 | 4.45 |
| Omrixate | 2.35 | 3.21 |
| Omrixate + SUV's | 2.31 | 3.90 |

Mixtures containing liposomes and FVIII from Baxter or Omrixate increased the half-life of the factor by 20%, when compared with the pharmacokinetic values of the free factor, as can be seen from the above table. The half-life of factor FVIII from Kogenate, mixed with E-PC/PEG-PE liposomes was twice as long as compared with the free factor form.

EXAMPLE 4

Methods and Materials

1. Liposome Preparation:

Liposomes were prepared as follows: Egg phosphatidyl choline (EPC) and distearoyl phosphatidyl-ethanolamine methyl polyethylene glycol 2000 (DSPE-PEG 2000) were weighed to a ratio of 80:20 w/w (5% molar ratio of DSPE-PEG 2000), respectively, dissolved to 10% w/v in tert-buthanol (Reidel-de Haen), and the solution was lyophilized. The obtained dry lipid powder was resuspended to 10% w/v in a buffer containing 130 mM NaCl, 10 mM sodium citrate, 1 mM $CaCl_2$ pH 7.0 to form liposomes. The liposomes were filtered in an extruder apparatus (Avestin) through polycarbonate filters 1.2 μm, 0.2 μm and 0.1 μm in size to form liposomes of 120–140 nm in size.

2. Liposome Quality Control

Quality control of the liposomes included:
1) Size distribution measured by sub-micron particle analyzer (N4 plus, Coulter Electronics).
2) Phospholipid determination (by phosphorus).
3) Chemical stability of the lipids by TLC.

The tests were performed as described in: Barenholz, Y. and Amselem, S. (1993) in Liposome Technology, 2nd edition, Vol. I (Gregoriadis, G., ed.), CRC Press, Boca Rayton, Fla., pp. 527–616.

3. Formulation of FVIII and Liposomes

Kogenate (Lot no. 70K027, 620 IU) or New Kogenate (500 IU) was dissolved in 1 ml or 2 ml of $H_2O$. The rFVIII-SQ concentrate was dissolved in liposome solution. Factor VIII was formulated with liposomes by mixing FVIII concentrate with the liposomes for about 1 hour at room temperature. The ratio of lipids to FVIII units was about 1 mg lipids/1 unit FVIII.

4. Injection into Hemophilic Mice and Bleeding Procedures

Factor VIII and FVIII formulated with liposomes were injected into the tail vein of hemophilic mice. The injected dose was 3 units/mouse for Kogenate (2 separate experiments) and New Kogenate and 4 units/mouse for rFVIII-SQ. The mice were bled into citrate tubes at 10 minutes after the injection and at about 4, 19 and 27 hours post-injection.

5. Measurement of FVIII Concentrate in Mouse Plasma

Human FVIII concentrate in mouse plasma was measured using a chromogenic assay (Chromogenix) according to the manufacturer's instructions, and by one stage clotting assay (using Stago reagents and ST4 clotting machine) according to the manufacturer's instructions.

6. Pharmacokinetics Analysis

Pharmacokinetics parameters were analyzed using a computer program (RSTRIP, MicroMath Inc.).

7. Survival of Hemophilic Mice Following a Tail Cut

Mice were injected with free rFVIII-SQ or liposome formulated rFVIII-SQ (4 units/mouse, 11 mice in each group. At 20 hours post injection 2 cm of the tail were cut. Tails of the surviving mice were cut again at 28, 44, 52, 69, 88 and 140 hours post-injection (2 mm each time).

Results

The results of FVIII activity at each time point post-injection and the pharmacokinetic parameters [FVIII half-life (HL) and the area under the curve (AUC)] of 4 different experiments are summarized in Tables 4–7B. In Tables 4 and 5, 3 units of Kogenate/mouse were injected; In Table 6, 3 units of New Kogenate/mouse were injected; and in Tables 7A, 7B, and in FIG. 1, 4 units of rFVIII-SQ/mouse were injected.

TABLE 4

Factor VIII activity (u/ml measured by a chromogenic assay) and pharmacokinetic parameters following injection of human FVIII into hemophilic mice

| Injected Material | | T = 10 min. | T = 4.5 hours | T = 19 hours | T = 27 hours | Area under the curve (AUC) (IU*h/ml) | Half life (HL) (h) |
|---|---|---|---|---|---|---|---|
| Kogenate (n = 7) | Average (u/ml) ± SD | 2.878 ± 0.571 | 0.450 ± 0.392 | 0.015 ± 0.0043 | 0.0016 ± 0.004 | 7.218 | 1.619 |
| | | | T = 3.6 Hours | T = 18.1 hours | T = 26.1 hours | | |
| Kogenate + liposomes (n = 7) | Average (u/ml) ± SD | 2.951 ± 0.333 | 1.121 ± 0.337 | 0.023 ± 0.003 | 0.014 ± 0.0018 | 10.969 | 2.460 |

TABLE 5

Factor VIII activity (u/ml measured by a chromogenic assay) and pharmacokinetic parameters following injection of human FVIII into hemophilic mice

| Injected Material | | T = 10 min. | | | | Area under the curve (AUC) (IU*h/ml) | Half life (HL) (h) |
|---|---|---|---|---|---|---|---|
| | | | T = 3.334 hours | T = 19.334 hours | T = 26.3 hours | | |
| Kogenate (n = 8) | Average (u/ml) ± SD | 3.686 ± 0.674 | 0.960 ± 0.469 | 0.0128 ± 0.007 | 0.0025 ± 0.006 | 9.314 | 1.632 |
| | | | T = 3.5 hours | T = 19.5 hours | T = 26.5 hours | | |
| Kogenate + liposomes (n = 8) | Average (u/ml) ± SD | 3.618 ± 0.982 | 1.571 ± 0.137 | 0.032 ± 0.009 | 0.012 ± 0.009 | 15.059 | 2.771 |

TABLE 6

Factor VIII activity (u/ml measured by a chromogenic assay) and pharmacokinetic parameters following injection of human FVIII into hemophilic mice

| Injected Material | | T = 10 min. | | | | Area under the curve (AUC) (IU*h/ml) | Half life (HL) (h) |
|---|---|---|---|---|---|---|---|
| | | | T = 2.5 hours | T = 17 hours | T = 26 hours | | |
| New Kogenate (n = 4) | Average (u/ml) ± SD | 1.841 ± 0.643 | 0.120 ± 0.036 | 0.004 ± 0.003 | 0.0015 ± 0.003 | 1.910 | 0.592 |
| | | | T = 2.666 hours | T = 17.166 hours | T = 26.166 hours | | |
| New Kogenate + liposomes (n = 6) | Average (u/ml) ± SD | 2.393 ± 0.243 | 0.352 ± 0.131 | 0.011 ± 0.0019 | 0.008 ± 0.001 | 3.544 | 0.904 |

TABLE 7A

Factor VIII activity (u/ml measured by a chromogenic assay) and pharmacokinetic parameters following injection of human FVIII into hemophilic mice

| Injected Material | | T = 10 min. | | | Area under the curve (AUC) (IU*h/ml) | Half life (HL) (h) |
|---|---|---|---|---|---|---|
| | | | T = 4.166 hours | T = 20.166 hours | | |
| RVIII (n = 10) | Average (u/ml) ± SD | 3.937 ± 0.449 | 0.444 ± 0.131 | 0 | 7.9 | 1.270 |
| | | | T = 4.5 hours | T = 20.5 hours | | |
| RVIII + liposomes (n = 11) | Average (u/ml) ± SD | 3.828 ± 1.08 | 0.555 ± 0.198 | 0.005 ± 0.008 | 9.249 | 1.555 |

TABLE 7B

Factor VIII activity (u/ml measured by a one stage clotting assay) and pharmacokinetic parameters following injection of human FVIII into hemophilic mice

| Injected Material | | T = 10 min. | | | Area under the curve (AUC) (IU*h/ml) | Half life (HL) (h) |
|---|---|---|---|---|---|---|
| | | | T = 4.166 hours | T = 20.166 hours | | |
| RVIII (n = 9) | Average (u/ml) ± SD | 4.181 ± 1.275 | 1.742 ± 0.778 | 0.414 ± 0.085 | 21.246 | 3.521 |
| | | | T = 4.5 hours | T = 20.5 hours | | |
| RVIII + liposomes (n = 10) | Average (u/ml) ± SD | 3.305 ± 0.831 | 2 ± 0.709 | 0.531 ± 0.147 | 28.718 | 6.900 |

In addition, the half-life of human FVIII in each mouse was calculated and the FVIII half-lives in all the experimental groups were statistically compared to each other by a student t-test.

The statistical analysis indicates that in all 4 experiments human FVIII half-lives in the groups that received liposome-formulated FVIII were higher and significantly different ($p<0.055$) from human FVIII half-lives in the groups that received free FVIII:

HL of Kogenate versus HL of Kogenate+liposomes (table 4) p=0.054;
HL of Kogenate versus AUC of Kogenate+liposomes (table 5) p=0.031;
HL of New Kogenate versus HL of New Kogenate+liposomes (table 6) p=0.0085;
HL of rFVIII-SQ versus HL of rFVIII-SQ+liposomes (table 7A) p=0.0045; HL of rFVIII-SQ versus HL of rFVIII-SQ+liposomes (table 7B) p=0.022).

These results indicate that the formulation of Kogenate, New Kogenate or rFVIII-SQ with liposomes significantly increases the factor half-life (HL) and the area under the curve (AUC) of FVIII in hemophilic mice (factor of 1.6–2.0 for HL and AUC).

Survival of the mice is illustrated in FIG. 1. The results of the tail cut experiment indicate that the liposome formulated FVIII is biologically active longer than free FVIII, and therefore can protect hemophilic patients for a longer period of time.

EXAMPLE 5

Effectiveness of FVIII Composition in Patients with Inhibitors 15 units of FVIII (Kogenate) were incubated for one hour at room temperature with 120 nm liposomes (15 mg lipids) containing EPC:DSPE-PEG2000 (95:5 mole %). Then, 1 unit of free FVIII (Kogenate) or 1 unit of liposome formulated FVIII were incubated for 2 hours at 37° C. with various dilutions of a serum from a hemophilia patient who had developed inhibitors (anti FVIII antibodies). After the incubation, the activity of factor VIII was measured by a chromogenic assay.

The results are summarized in table 8:

TABLE 8

Activity (units/ml) of factor VIII in the presence of FVIII inhibitors

| Serum dilution | Free FVIII | FVIII-liposomes |
| --- | --- | --- |
| None | 0 | 0.028 |
| 1:5 | 0.052 | 0.094 |
| 1:10 | 0.137 | 0.162 |
| 1:25 | 0.6 | 0.98 |
| 1:100 | 8.736 | 14.94 |

It can clearly be seen from this experiment that administration of FVIII together with the colloidal particles is effective in protecting the FVIII from serum inhibitors.

What is claimed is:

1. A pharmaceutical composition for parenteral administration comprising a therapeutically effective amount of a therapeutic protein or polypeptide and substantially neutral colloidal particles, said particles comprising approximately 1–20 mole percent of an amphipathic lipid derivatized with a biocompatible hydrophilic polymer, said polymer carrying substantially no net charge, wherein said protein or polypeptide is selected from the group consisting of:

(a) proteins or polypeptides capable of externally binding said colloidal particles; and
(b) proteins or polypeptides capable of binding polyethylene glycol, wherein said protein or polypeptide is not encapsulated in said colloidal particles and is non-covalently bound thereto, and wherein no therapeutic component is encapsulated in said colloidal particles.

2. The pharmaceutical composition of claim 1 wherein the colloidal particles have a mean particle diameter of about 0.05 to about 0.4 microns.

3. The pharmaceutical composition of claim 2 wherein the colloidal particles have mean particle diameter of approximately 0.1 microns.

4. The pharmaceutical composition of claim 1 wherein said amphipathic lipid is a phospholipid from natural or synthetic sources.

5. The pharmaceutical composition of claim 4 wherein said amphipathic lipid is phosphatidylethanolamine (PE).

6. The pharmaceutical composition of claim 1 wherein said biocompatible hydrophilic polymer is selected from the group consisting of polyalkylether, polylactic and polyglycolic acid families.

7. The pharmaceutical composition of claim 6 wherein said biocompatible hydrophilic polymer is polyethylene glycol.

8. The pharmaceutical composition of claim 7 wherein the polyethylene glycol has a molecular weight of about 1000 to about 5000 daltons.

9. The pharmaceutical composition of claim 8 wherein the polyethylene glycol has a molecular weight of approximately 2000 daltons.

10. The pharmaceutical composition of claim 1 wherein said colloidal particles further comprise a second amphipathic lipid obtained from either natural or synthetic sources.

11. The pharmaceutical composition of claim 10 wherein said second amphipathic lipid is phosphatidylcholine.

12. The pharmaceutical composition of claim 11, wherein the amphipathic lipid that is derivatized with a biocompatible hydrophilic polymer is phosphatidylethanolamine (PE).

13. A method of administering a therapeutically effective amount of a therapeutic protein or polypeptide to a patient, comprising parenteral administration of substantially neutral colloidal particles with said therapeutic protein or polypeptide non-covalently bound thereto, wherein:

(1) said colloidal particles comprise approximately 1–20 mole percent of an amphipathic lipid derivatized with a biocompatible hydrophilic polymer, said polymer carrying substantially no net charge;

(2) said protein or polypeptide is selected from the group consisting of:

(a) proteins or polypeptides capable of externally binding said colloidal particles; and
(b) proteins or polypeptides capable of binding polyethylene glycol, (3) said protein or polypeptide is not encapsulated in said colloidal particles, and (4) no therapeutic component is encapsulated in said colloidal particles.

14. The method of claim 13, wherein the colloidal particles have a mean particle diameter of about 0.05 to about 0.4 microns.

15. The method of claim 13, wherein said amphipathic lipid is a phospholipid from natural or synthetic sources.

16. The method of claim 13, wherein said colloidal particles further comprise a second amphipathic lipid obtained from either natural or synthetic sources.

17. The method of claim 16, wherein the amphipathic lipid that is derivatized with a biocompatible hydrophilic polymer is phosphatidylethanolamine (PE) and the second amphipathic lipid is phosphatidylcholine.

* * * * *